United States Patent
Kuretake et al.

(10) Patent No.: US 11,642,661 B2
(45) Date of Patent: May 9, 2023

(54) SUPPORTED CATALYST FOR ORGANIC SUBSTANCE DECOMPOSITION AND ORGANIC SUBSTANCE DECOMPOSITION DEVICE

(71) Applicant: Murata Manufacturing Co., Ltd., Nagaokakyo (JP)

(72) Inventors: Satoshi Kuretake, Nagaokakyo (JP); Kentaro Ishihara, Nagaokakyo (JP); Nario Sugahara, Nagaokakyo (JP)

(73) Assignee: MURATA MANUFACTURING CO., LTD., Nagaokakyo (JP)

( * ) Notice: Subject to any disclaimer, the term of this patent is extended or adjusted under 35 U.S.C. 154(b) by 240 days.

(21) Appl. No.: 17/093,849

(22) Filed: Nov. 10, 2020

(65) Prior Publication Data
US 2021/0053030 A1    Feb. 25, 2021

Related U.S. Application Data

(63) Continuation of application No. PCT/JP2019/008593, filed on Mar. 5, 2019.

(30) Foreign Application Priority Data

May 11, 2018    (JP) .............................. JP2018-092386

(51) Int. Cl.
*B01J 23/889*     (2006.01)
*A61L 9/03*     (2006.01)
(Continued)

(52) U.S. Cl.
CPC ............. *B01J 23/8892* (2013.01); *A61L 9/03* (2013.01); *B01D 53/865* (2013.01);
(Continued)

(58) Field of Classification Search
CPC .... B01J 23/8892; B01J 21/066; B01J 23/002; B01J 23/34; B01J 23/688; B01J 23/78;
(Continued)

(56) References Cited

U.S. PATENT DOCUMENTS

| | | |
|---|---|---|
| 3,644,147 A | 2/1972 | Young, II |
| 5,380,692 A | 1/1995 | Nakatsuji et al. |

(Continued)

FOREIGN PATENT DOCUMENTS

| | | | | |
|---|---|---|---|---|
| EP | 2374526 A1 | * | 10/2011 | ......... B01D 67/0041 |
| JP | 07080310 A | * | 3/1995 | |

(Continued)

OTHER PUBLICATIONS

Yuxi Liu et al.; "Controlled preparation and high catalytic performance of three-dimensionally ordered macroporous LaMnO3 with nanovoid skeletons for the combustion of toluene"; Journal of Catalysis 287, 2012, pp. 149-160.

(Continued)

*Primary Examiner* — Anthony J Zimmer
*Assistant Examiner* — Logan Edward Laclair
(74) *Attorney, Agent, or Firm* — ArentFox Schiff LLP

(57) ABSTRACT

A supported catalyst for decomposing an organic substance that includes a support and a catalyst particle supported on the support. The catalyst particle contains a perovskite-type composite oxide represented by $A_xB_yM_zO_w$, where the A contains at least one selected from Ba and Sr, the B contains Zr, the M is at least one selected from Mn, Co, Ni and Fe, y+z=1, x≥0.995, z≤0.4, and w is a positive value satisfying electrical neutrality. A film thickness of a catalyst-supporting film supported on the support and containing the catalyst particle is 5 μm or more, or a supported amount as deter- (Continued)

mined by normalizing a mass of the catalyst particle supported on the support by a volume of the support is 45 g/L or more.

18 Claims, 5 Drawing Sheets

(51) Int. Cl.
| | |
|---|---|
| B01D 53/86 | (2006.01) |
| B01J 23/00 | (2006.01) |
| B01J 23/34 | (2006.01) |
| B01J 23/68 | (2006.01) |
| B01J 23/78 | (2006.01) |
| B01J 35/10 | (2006.01) |
| C01G 45/12 | (2006.01) |
| C01G 51/00 | (2006.01) |
| C01G 53/00 | (2006.01) |
| B01J 21/06 | (2006.01) |
| B01J 35/04 | (2006.01) |
| B01D 53/94 | (2006.01) |
| B01J 21/04 | (2006.01) |
| B01J 35/02 | (2006.01) |
| B01J 37/00 | (2006.01) |
| B01J 21/16 | (2006.01) |

(52) U.S. Cl.
CPC ..... *B01D 53/8668* (2013.01); *B01D 53/8687* (2013.01); *B01D 53/8696* (2013.01); *B01D 53/94* (2013.01); *B01J 21/04* (2013.01); *B01J 21/066* (2013.01); *B01J 23/002* (2013.01); *B01J 23/34* (2013.01); *B01J 23/688* (2013.01); *B01J 23/78* (2013.01); *B01J 35/026* (2013.01); *B01J 35/04* (2013.01); *B01J 35/1009* (2013.01); *B01J 35/1038* (2013.01); *B01J 35/1061* (2013.01); *B01J 35/1066* (2013.01); *B01J 35/1071* (2013.01); *B01J 35/1076* (2013.01); *C01G 45/125* (2013.01); *C01G 45/1207* (2013.01); *C01G 51/66* (2013.01); *C01G 53/66* (2013.01); *B01D 2255/104* (2013.01); *B01D 2255/2042* (2013.01); *B01D 2255/2047* (2013.01); *B01D 2255/2061* (2013.01); *B01D 2255/2063* (2013.01); *B01D 2255/2073* (2013.01); *B01D 2255/2092* (2013.01); *B01D 2255/2094* (2013.01); *B01D 2255/20707* (2013.01); *B01D 2255/20715* (2013.01); *B01D 2255/20738* (2013.01); *B01D 2255/20746* (2013.01); *B01D 2255/20753* (2013.01); *B01D 2255/20792* (2013.01); *B01D 2255/402* (2013.01); *B01D 2255/9202* (2013.01); *B01D 2255/9207* (2013.01); *B01D 2257/7027* (2013.01); *B01D 2258/01* (2013.01); *B01D 2258/02* (2013.01); *B01J 21/16* (2013.01); *B01J 37/009* (2013.01); *C01P 2002/34* (2013.01); *C01P 2002/50* (2013.01); *C01P 2002/72* (2013.01); *C01P 2002/77* (2013.01); *C01P 2006/12* (2013.01); *C01P 2006/14* (2013.01); *C01P 2006/16* (2013.01)

(58) Field of Classification Search
CPC ...... B01J 35/026; B01J 35/04; B01J 35/1009; B01J 35/1038; B01J 35/1061; B01J 21/16; B01J 2523/00; A61L 9/03; A61L 9/00; A61L 9/01; B01D 53/865; B01D 53/8668; B01D 53/8696; B01D 53/94; B01D 2255/2042; B01D 2255/20715; B01D 2255/2073; B01D 2255/20738; B01D 2255/20746; B01D 2255/20753; B01D 2255/20792; B01D 2255/402; B01D 2255/9207; B01D 2258/01; B01D 2258/02; B01D 53/86; C01G 45/1207; C01G 45/125; C01G 51/66; C01G 53/66; C01P 2002/34; C01P 2002/50; C01P 2006/12; C01P 2006/14; C01P 2006/16
See application file for complete search history.

(56) References Cited

U.S. PATENT DOCUMENTS

| | | | |
|---|---|---|---|
| 6,060,420 | A | 5/2000 | Munakata et al. |
| 8,123,931 | B2 | 2/2012 | Kang et al. |
| 8,329,612 | B2 | 12/2012 | Sato et al. |
| 8,569,200 | B2 | 10/2013 | Kang et al. |
| 2002/0035035 | A1 | 3/2002 | Kirchnerova et al. |
| 2007/0027031 | A1 | 2/2007 | Ikeda et al. |
| 2007/0249497 | A1 | 10/2007 | Tanaka et al. |
| 2009/0108239 | A1* | 4/2009 | Caro ................. C01B 3/386 428/688 |
| 2009/0131252 | A1 | 5/2009 | Tanaka et al. |
| 2009/0286677 | A1 | 11/2009 | Takeshima et al. |
| 2009/0286680 | A1 | 11/2009 | Hirano et al. |
| 2010/0139152 | A1 | 6/2010 | Hucul et al. |
| 2012/0074357 | A1 | 3/2012 | Sato et al. |
| 2016/0115835 | A1 | 4/2016 | Daido et al. |

FOREIGN PATENT DOCUMENTS

| | | |
|---|---|---|
| JP | H0780310 A | 3/1995 |
| JP | 2000140635 A | 5/2000 |
| JP | 3406001 B2 | 5/2003 |
| JP | 2006231280 A | 9/2006 |
| JP | 2006346603 A | 12/2006 |
| JP | 2006347825 A | 12/2006 |
| JP | 5076377 B2 | 11/2012 |
| JP | 2013244479 A | 12/2013 |
| JP | 2015229137 A | 12/2015 |
| JP | 6036276 B2 | 11/2016 |
| WO | 0016900 A1 | 3/2000 |
| WO | 2004096436 A1 | 11/2004 |
| WO | 2005058490 A1 | 6/2005 |
| WO | 2010143676 A1 | 12/2010 |
| WO | 2014189115 A1 | 11/2014 |
| WO | 2015194451 A1 | 12/2015 |

OTHER PUBLICATIONS

Japanese Office Action issued for Japanese Application No. 2020-518162, dated Jun. 29, 2021.
International Search Report issued for PCT/JP2018/045261, dated Feb. 5, 2018.
Kirchenerova, J. et al.; "Design criteria for high-temperature combustion catalysts"; Catalysis Letters, Jul. 2000, vol. 67, No. 2-4, pp. 175-181.
International Search Report issued for PCT/JP2019/017674, dated Jul. 16, 2019.
International Search Report issued for PCT/JP2019/015483, dated Jul. 16, 2019.
International Search Report issued for PCT/JP2019/008692, dated May 21, 2019.
International Search Report issued for PCT/JP2019/008592, dated May 21, 2019.
Written Opinion of the International Searching Authority issued for PCT/JP2019/008593, dated May 21, 2019.
Written Opinion of the International Searching Authority issued for PCT/JP2019/008592, dated May 21, 2019.
Written Opinion of the International Searching Authority issued for PCT/JP2019/015483, dated Jul. 16, 2019.
Written Opinion of the International Searching Authority issued for PCT/JP2019/017674, dated Jul. 16, 2019.

(56) References Cited

OTHER PUBLICATIONS

Written Opinion of the International Searching Authority issued for PCT/JP2018/045261, dated Feb. 5, 2019.
Gallucci, Katia et al.; "Catalytic combustion of methane on $BaZr_{(1-x)}Me_xO_3$ perovskites synthesized by a modified citrate method"; Catalysis Today, 2012, vol. 197, No. 1, pp. 236-242.
Tuyen, Nguyen Van et al.; "Interaction of Hydrogen with Perovskite-supported Metal Catalysts: I. $M/Sr_{1-x}Zr_{1-y}O_{3-a}$ (M=Cu, Pd)"; Kinetics and Catalysis, 1996, vol. 37, No. 4, pp. 575-578.

\* cited by examiner

SUPPORTED CATALYST FOR ORGANIC SUBSTANCE DECOMPOSITION AND ORGANIC SUBSTANCE DECOMPOSITION DEVICE

CROSS REFERENCE TO RELATED APPLICATIONS

The present application is a continuation of International application No. PCT/JP2019/008593, filed Mar. 5, 2019, which claims priority to Japanese Patent Application No. 2018-092386, filed May 11, 2018, the entire contents of each of which are incorporated herein by reference.

FIELD OF THE INVENTION

The present invention relates to a supported catalyst for decomposing an organic substance, and an organic substance decomposition device including the supported catalyst for decomposing an organic substance.

BACKGROUND OF THE INVENTION

Conventionally, catalysts for decomposing an organic substance have been known.
Patent Document 1 (Japanese Patent No. 6303834) describes a catalyst for decomposing an organic substance that does not contain a precious metal and rare earth elements and exhibits less deterioration even when being heat-treated at 800° C. for 100 hours.

SUMMARY OF THE INVENTION

It has been found that when the catalyst for decomposing an organic substance described in Patent Document 1 is supported on a support, deterioration of the catalyst after heat treatment at high temperature becomes significant depending on the supported amount of the catalyst or the film thickness of a supporting film.

To solve the above-described problems, an object of the present invention is to provide a supported catalyst for decomposing an organic substance that can prevent deterioration due to heat treatment at high temperature, and an organic substance decomposition device including such a supported catalyst for decomposing an organic substance.

The supported catalyst for decomposing an organic substance of a first aspect of the present invention includes a support; and a catalyst-supporting film supported on the support, the catalyst-supporting film containing a catalyst particle, and the catalyst-supporting film having a film thickness of 5 μm or more, wherein the catalyst particle contains a perovskite-type composite oxide represented by $A_xB_yM_zO_w$, where the A contains at least one selected from Ba and Sr, the B contains Zr, the M is at least one selected from Mn, Co, Ni and Fe, y+z=1, x≥0.995, z≤0.4, and w is a positive value satisfying electrical neutrality.

The film thickness of the catalyst-supporting film may be 116 μm or less.

The supported catalyst for decomposing an organic substance of a second aspect of the present invention includes a support; and a catalyst particle supported on the support, wherein the catalyst particle contains a perovskite-type composite oxide represented by $A_xB_yM_zO_w$, where the A contains at least one selected from Ba and Sr, the B contains Zr, the M is at least one selected from Mn, Co, Ni and Fe, y+z=1, x≥0.995, z≤0.4, w is a positive value satisfying electrical neutrality, and a supported amount as determined by normalizing a mass of the catalyst particle supported on the support by a volume of the support is 45 g/L or more.

The supported amount may be 45 g/L to 530 g/L.

The x and the z may respectively satisfy 1.001≤x≤1.05 and 0.05≤z≤0.2.

Further, the x may satisfy x≥1.005.

Further, the z may satisfy z≤0.1.

A decomposition rate after the supported catalyst for decomposing an organic substance is heat-treated at 950° C. for 48 hours may be more than 0.9 when the decomposition rate before the heat treatment is defined as 1.

The support may be a porous structure containing a plurality of pores, each of the plurality of pores having a diameter of 0.3 μm to 50 μm.

The support may contain cordierite.

An organic substance decomposition device of the present invention includes the above-described supported catalyst for decomposing an organic substance according to the first aspect or the second aspect of the present invention.

According to the supported catalyst for decomposing an organic substance of the present invention, deterioration due to heat treatment at high temperature can be prevented.

Further, the organic substance decomposition device of the present invention includes a supported catalyst for decomposing an organic substance that can prevent deterioration due to heat treatment at high temperature, and thus is excellent in organic substance decomposition characteristics.

DETAILED DESCRIPTION OF THE PREFERRED EMBODIMENTS

Figure 1:
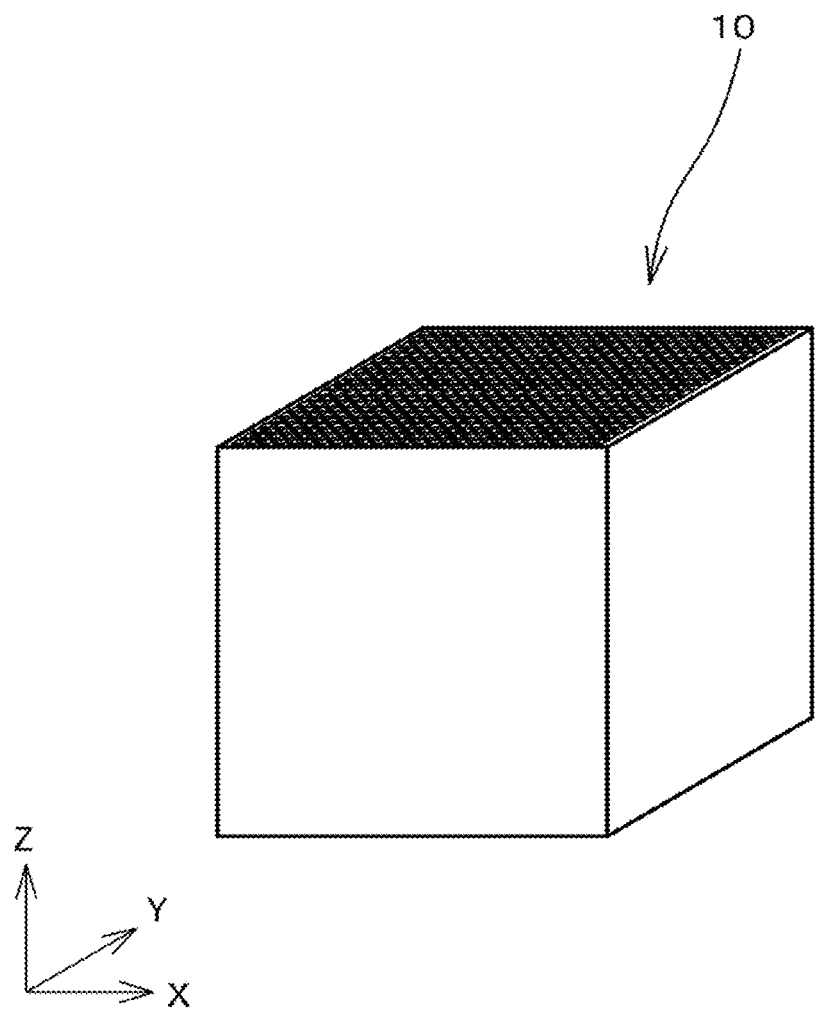
FIG. 1 is a perspective view illustrating an appearance shape of honeycomb ceramics.

Embodiments of the present invention will be shown below, and features of the present invention will be specifically described.

The supported catalyst for decomposing an organic substance according to the present invention satisfies at least one of the following first requirement (hereinafter, referred to as the first requirement of the present invention) and second requirement (hereinafter, referred to as the second requirement of the present invention).

The supported catalyst for decomposing an organic substance that satisfies the first requirement of the present invention includes: a support; a catalyst-supporting film supported on the support, the catalyst-supporting film containing a catalyst particle, and the catalyst-supporting film having a film thickness of 5 μm or more, wherein the catalyst particle contains a perovskite-type composite oxide represented by $A_xB_yM_zO_w$, where the A contains at least one selected from Ba and Sr, the B contains Zr, the M is at least one selected from Mn, Co, Ni and Fe, y+z=1, x≥0.995, z≤0.4, and w is a positive value satisfying electrical neutrality.

Further, the supported catalyst for decomposing an organic substance that satisfies the second requirement of the present invention includes a support; and a catalyst particle supported on the support, wherein the catalyst particle contains a perovskite-type composite oxide represented by $A_xB_yM_zO_w$, where the A contains at least one selected from Ba and Sr, the B contains Zr, the M is at least one selected from Mn, Co, Ni and Fe, y+z=1, x≥0.995, z≤0.4, and w is a positive value satisfying electrical neutrality; and a supported amount as determined by normalizing a mass of the catalyst particle supported on the support by a volume of the support is 45 g/L or more.

A supported catalyst for decomposing an organic substance that satisfies the above-described first requirement or second requirement of the present invention can prevent deterioration due to heat treatment at high temperature as described later. This supported catalyst for decomposing an organic substance can be used for various applications for decomposition of organic substances, such as purification of exhaust gas discharged from factories or automobiles. In this case, it is possible to configure an organic substance decomposition device including a supported catalyst for decomposing an organic substance that satisfies the first requirement or the second requirement of the present invention.

Example 1

Powders of high-purity $BaCO_3$, $ZrO_2$, and $MnCO_3$ were each weighed so as to be the composition shown in Table 1, pure water was added thereto. This was wet-mixed with $ZrO_2$ cobblestones, thus preparing a slurry. The slurry was dried at 120° C. by a dryer, and then the obtained powder was heat-treated at 1,100° C. for 2 hours, thus preparing a targeted perovskite-type composite oxide.

Subsequently, to obtain a catalyst slurry for supporting, to a predetermined weight of the perovskite-type compound shown in Table 1, 320 g of pure water was added, and appropriate amounts of an organic dispersant and antifoaming agent were further added. This was wet-mixed with $ZrO_2$ cobblestones for 2 hours, thus preparing a catalyst slurry. An inorganic sol was not used in preparation of the catalyst slurry.

A piece of honeycomb ceramics serving as a support was immersed in the obtained catalyst slurry for one minute. The honeycomb ceramics contains cordierite. In this embodiment, the honeycomb ceramics is composed of porous cordierite.

FIG. 1 is a perspective view illustrating an appearance shape of honeycomb ceramics 10. Also, FIG. 2 is a partial enlarged schematic view of the honeycomb ceramics 10 of FIG. 1 as viewed in the Z-axis direction.

For the size of the honeycomb ceramics 10, the dimension in the X-axis direction of FIG. 1 is approximately 40 mm, the dimension in the Y-axis direction is approximately 40 mm, and the dimension in the Z-axis direction is approximately 50 mm. The honeycomb ceramics 10 is provided with a plurality of cells 11. The size of the cell in the Z-axis direction in a plan view is approximately 1.5 mm×approximately 1.5 mm, and the number of cells per square inch is approximately 200.

Figure 2:
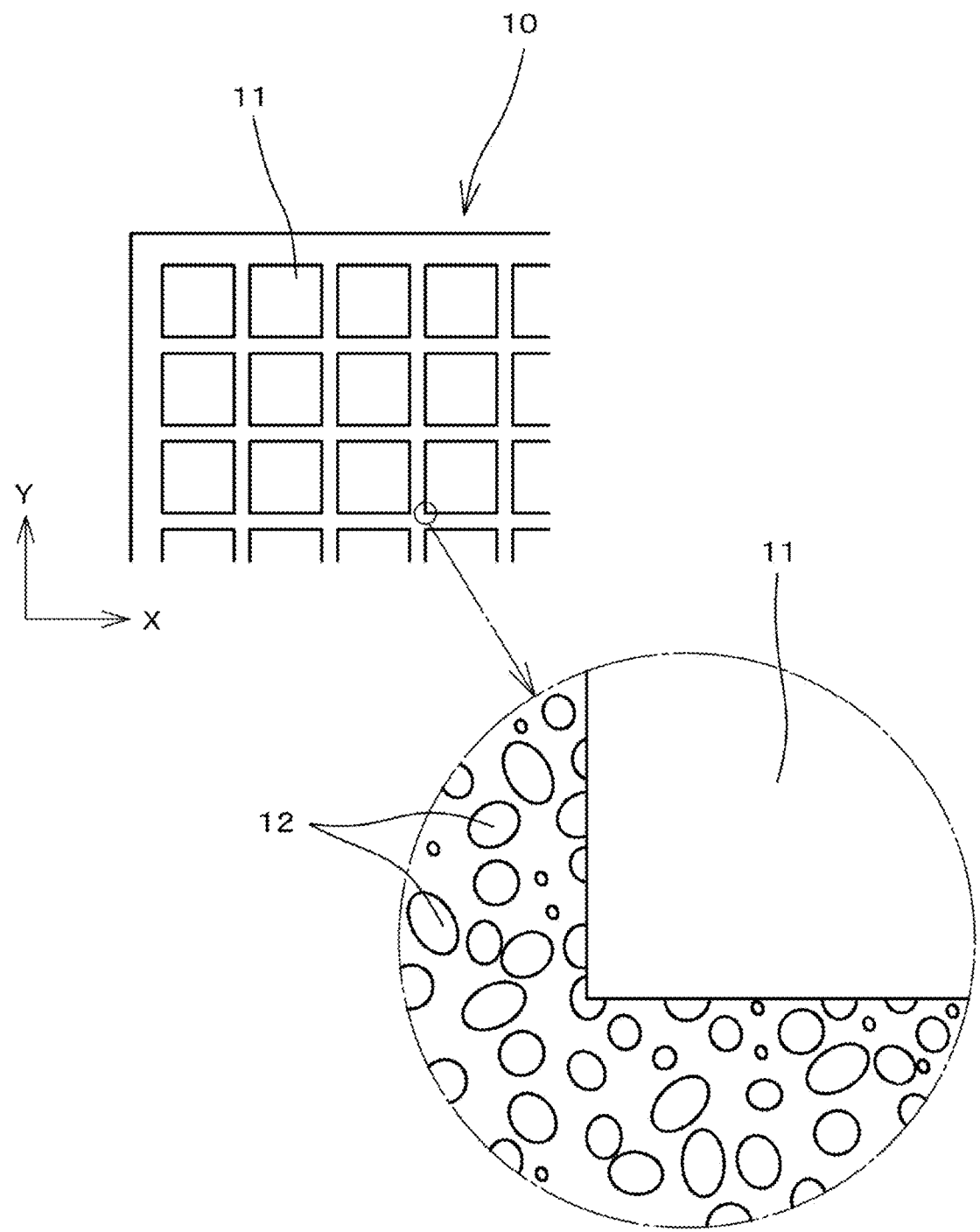
FIG. 2 is a partial enlarged schematic view of the honeycomb ceramics of FIG. 1 as viewed in the Z-axis direction.

As shown in FIG. 2, portions of the honeycomb ceramics 10 other than the cells 11 are provided with a number of pores 12. In other words, the honeycomb ceramics 10 is a porous structure containing a plurality of pores 12. The pore 12 has a function of causing porous cordierite to absorb moisture contained in a catalyst slurry when the catalyst slurry is applied to the honeycomb ceramics 10. That is, moisture contained in the catalyst slurry is absorbed in the porous cordierite due to the capillary absorption force of the pore 12, and the concentration of the catalyst particle increases. Thus, a catalyst-supporting film, in which catalyst particles closely contact the inner walls of the cells, can be formed.

In this embodiment, the diameter of the pore 12 of the honeycomb ceramics which is a support is, for example, 0.3 μm to 50 μm, the average diameter is 3 μm, and the volumetric porosity is approximately 50%. The diameter of the pore 12 is a diameter of the equivalent circle. The above-described diameter of the pore 12 and the like are a value determined by a mercury intrusion method under the condition of mercury contact angle of 130°, mercury surface tension of 485 mN/m, and measurement pressure range of 3.45 kPa to 414 MPa.

Note that, in the present invention, the support is not limited to the honeycomb ceramics, and the diameter, the average diameter, and the volumetric porosity of the pore 12 of the support are not limited to the above-described numerical values.

After immersion in the catalyst slurry, an extra catalyst slurry remaining in the honeycomb ceramics was blown off by an air flow, and then the honeycomb ceramics was dried at 120° C. for 12 hours by a dryer. Thereafter, the honeycomb ceramics was fired at 950° C. or 1,050° C. for 3 hours in an air atmosphere by an electric furnace, thus obtaining a fired product which is a supported catalyst for organic substance decomposition. In this fired product, catalyst particles are supported on the inner walls of cells of the honeycomb ceramics serving as a support.

Figure 3:
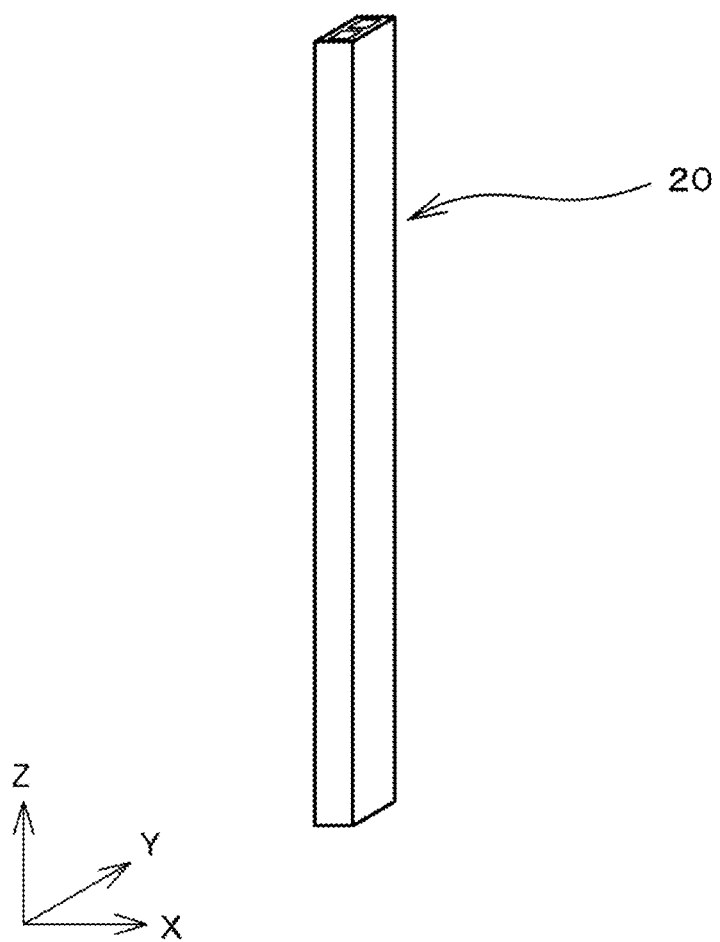
FIG. 3 is a perspective view illustrating an appearance shape of a supporting honeycomb sample.

Subsequently, a stick-like piece including two cells was cut out from the obtained fired product, and an extra catalyst attached to the peripheral part of the stick-like piece was scraped off with sandpaper, thus preparing a supporting honeycomb sample. FIG. 3 is a perspective view illustrating an appearance shape of a supporting honeycomb sample 20. The dimension of the supporting honeycomb sample 20 in the X-axis direction is approximately 2 mm, the dimension in the Y-axis direction is approximately 4 mm, and the dimension in the Z-axis direction is approximately 50 mm.

Further, to examine the characteristics after performing heat treatment at high temperature, a part of the supporting honeycomb sample 20 was further subjected to additional heat treatment at 950° C. for 48 hours by an electric furnace.

Supporting honeycomb samples for activity evaluation before and after additional heat treatment were obtained by the above-described method.

<Activity Evaluation Method>

The activity evaluation method of the supporting honeycomb sample will be described.

(1) Test Apparatus

Figure 4:
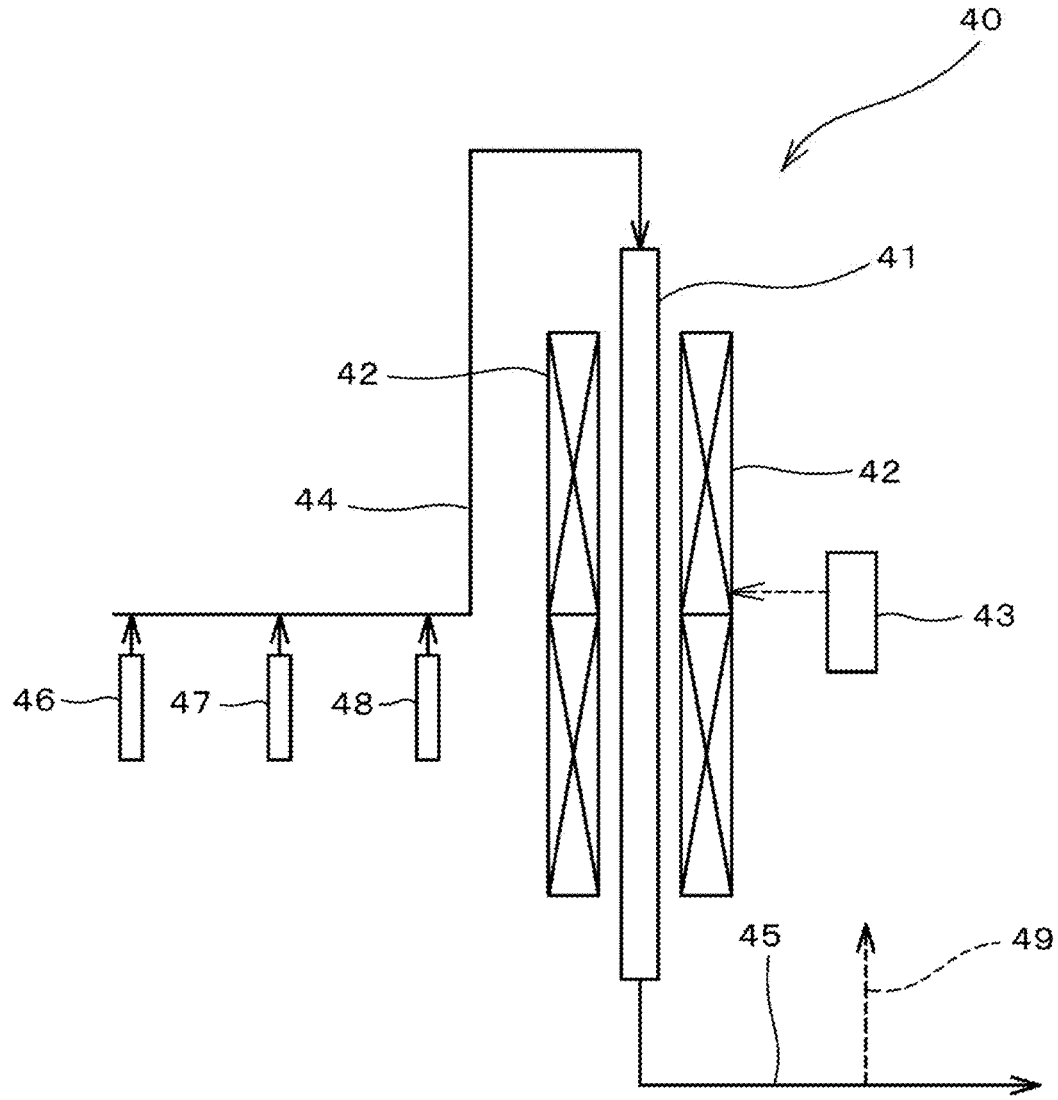
FIG. 4 is a schematic block diagram of a test apparatus used for evaluating the organic substance decomposition performance of a supported catalyst for decomposing an organic substance.

FIG. 4 is a schematic block diagram of a test apparatus 40 used for evaluating the organic substance decomposition performance of a supported catalyst for organic substance decomposition. The test apparatus 40 includes a tube 41 through which an organic substance flows, heating units 42 for heating the organic substance that flows through the tube 41, and a control unit 43 that controls the heating unit 42.

The supporting honeycomb sample prepared by the above-described method is disposed in a region inside the tube 41 heated by the heating units 42.

Figure 5:
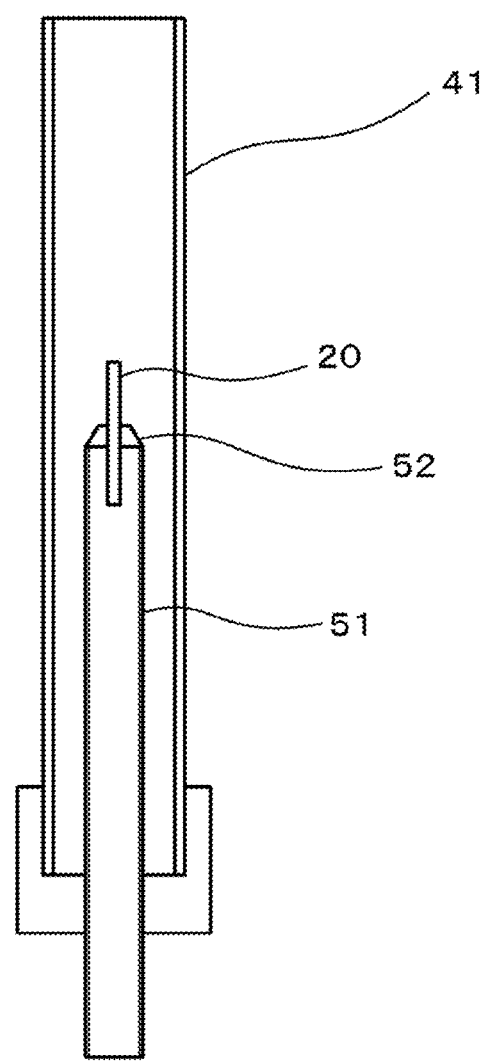
FIG. 5 is a sectional view for explaining a method of disposing a supporting honeycomb sample inside a tube.

FIG. 5 is a sectional view for explaining a method of disposing the supporting honeycomb sample 20 inside the tube 41. Approximately half the entire length of the supporting honeycomb sample 20 was inserted in a reaction tube 51 with a size of ¼ inch. Then, the supporting honeycomb sample 20 in this state was fixed and sealed using a heat-resistant inorganic adhesive 52. The reaction tube 51, in which the supporting honeycomb sample 20 has been inserted, was inserted inside the tube 41 with a size of ½ inch.

Note that the tube 41 and the reaction tube 51 have a double-tube structure, and a gas to be treated, which is supplied to the tube 41, passes through only inside the supporting honeycomb sample 20 and is discharged to a gas discharge tube 45 described later.

As shown in FIG. 4, a gas supply tube 44 is connected to the upstream side of the tube 41. A toluene supply line 46 for supplying toluene (organic substance), a nitrogen supply line 47 for supplying nitrogen ($N_2$), and an oxygen supply line 48 for supplying oxygen ($O_2$) are connected to the gas supply tube 44. In other words, a gas to be treated, which contains toluene, nitrogen, and oxygen, is supplied to the tube 41 via the gas supply tube 44.

The gas discharge tube 45 for discharging the treated gas after the organic substance has been decomposed by the supporting honeycomb sample 20 disposed inside the tube 41 to the outside of the system is connected to the downstream side of the tube 41. A sampling line 49 for sampling the treated gas is connected to the gas discharge tube 45, and is configured to analyze the concentration of toluene in the treated gas by gas chromatograph.

The control unit 43 is configured so as to control the temperature of a region heated by the heating unit 42.

(2) Test Method

Using the above-described test apparatus 40, a test was performed in which a gas to be treated which contains toluene, nitrogen, and oxygen, is continuously supplied to the tube 41 to decompose toluene. The composition of the gas to be treated was set such that toluene ($C_7H_8$): 50 ppm, nitrogen ($N_2$): 80 vol %, and oxygen ($O_2$): 20 vol %. The space velocity SV at a time of measurement was 30,000 (/h), and the catalyst temperature was 400° C.

The treated gas was sampled at an outlet of the sampling line 49, and the concentration of toluene was then determined though analysis by gas chromatograph. Then, the toluene decomposition rate was determined on the basis of the following Equation (1).

$$\text{Toluene decomposition rate (\%)}=100-100\times(\text{toluene concentration}/50) \quad (1)$$

Further, a deterioration rate of the toluene decomposition rate due to additional heat treatment when a toluene decomposition rate in a case of using a supporting honeycomb sample 20 before additional heat treatment is defined as C1, and a toluene decomposition rate in a case of using a supporting honeycomb sample 20 after additional heat treatment is defined as C2 was calculated from the following Equation (2).

$$\text{Deterioration rate (\%)}=100-100\times(C2/C1) \quad (2)$$

Subsequently, a method of measuring the film thickness of a catalyst-supporting film composed of catalyst particles supported on the honeycomb ceramics will be described.

A surface defined by the Y-axis direction and Z-axis direction of a stick-like supporting honeycomb sample prepared by a method similar to the above-described method is polished by approximately 1 mm with #400 sandpaper. The polished supporting honeycomb sample was observed from a direction orthogonal to the polished surface by an optical microscope, and the film thickness of the catalyst-supporting film adhered on the inner wall of the cell is measured using a function of distance measurement between two points. The film thickness was measured at five positions located at equal intervals along the Z-axis direction, and the average value thereof was determined.

Table 1 shows the characteristics of the prepared supported catalysts for decomposing an organic substance of sample Nos. 1 to 12.

TABLE 1

| Sample No. | Catalyst Preparation compositional ratio | | | | A(x) | | B(y) | M(z) | | | | Catalyst slurry Compound | Pure water |
|---|---|---|---|---|---|---|---|---|---|---|---|---|---|
| | x | y | z | y + z | Ba | Sr | Zr | Mn | Co | Ni | Fe | g | g |
| 1 | 1.010 | 0.900 | 0.100 | 1.000 | 1.000 | | 1.000 | 1.000 | | | | 220 | 320 |
| 2 | 1.010 | 0.900 | 0.100 | 1.000 | 1.000 | | 1.000 | 1.000 | | | | 270 | 320 |
| 3 | 1.010 | 0.900 | 0.100 | 1.000 | 1.000 | | 1.000 | 1.000 | | | | 350 | 320 |
| 4 | 1.010 | 0.900 | 0.100 | 1.000 | 1.000 | | 1.000 | 1.000 | | | | 450 | 320 |
| 5 | 1.010 | 0.900 | 0.100 | 1.000 | 1.000 | | 1.000 | 1.000 | | | | 550 | 320 |
| 6 | 1.010 | 0.900 | 0.100 | 1.000 | 1.000 | | 1.000 | 1.000 | | | | 650 | 320 |
| 7 | 1.010 | 0.900 | 0.100 | 1.000 | 1.000 | | 1.000 | 1.000 | | | | 220 | 320 |
| 8 | 1.010 | 0.900 | 0.100 | 1.000 | 1.000 | | 1.000 | 1.000 | | | | 270 | 320 |
| 9 | 1.010 | 0.900 | 0.100 | 1.000 | 1.000 | | 1.000 | 1.000 | | | | 350 | 320 |
| 10 | 1.010 | 0.900 | 0.100 | 1.000 | 1.000 | | 1.000 | 1.000 | | | | 450 | 320 |
| 11 | 1.010 | 0.900 | 0.100 | 1.000 | 1.000 | | 1.000 | 1.000 | | | | 550 | 320 |
| 12 | 1.010 | 0.900 | 0.100 | 1.000 | 1.000 | | 1.000 | 1.000 | | | | 650 | 320 |

| Sample No. | Firing temperature | Before additional heat treatment Supported amount of catalyst g/L | Film thickness | Decomposition rate % | After additional heat treatment Decomposition rate % | Deterioration rate % |
|---|---|---|---|---|---|---|
| 1 | 950° C. | 20 | 1 | 61.2 | 48.6 | 20.6 |
| 2 | 950° C. | 45 | 5 | 97.6 | 97.1 | 0.5 |

TABLE 1-continued

| | | | | | | |
|---|---|---|---|---|---|---|
| 3 | 950° C. | 118 | 18 | 98.8 | 98.7 | 0.1 |
| 4 | 950° C. | 193 | 35 | 99.4 | 99.4 | 0.0 |
| 5 | 950° C. | 326 | 73 | 99.2 | 99.1 | 0.1 |
| 6 | 950° C. | 450 | 110 | 99 | 99 | 0.0 |
| 7 | 1050° C. | 38 | 2 | 79 | 67.6 | 14.4 |
| 8 | 1050° C. | 65 | 6 | 96.9 | 96 | 0.9 |
| 9 | 1050° C. | 90 | 12 | 97.6 | 96.8 | 0.8 |
| 10 | 1050° C. | 200 | 36 | 97.9 | 97.6 | 0.3 |
| 11 | 1050° C. | 302 | 60 | 99.1 | 99.1 | 0.0 |
| 12 | 1050° C. | 530 | 116 | 98.8 | 98.7 | 0.1 |

Table 1 shows the composition of the catalyst, the amounts of the perovskite-type compound and pure water used for obtaining the catalyst slurry for supporting, the firing temperature, the supported amount and decomposition rate of the catalyst particle in the supported catalyst before additional heat treatment, and the decomposition rate and deterioration rate of the supported catalyst after additional heat treatment. In the supported amount of the catalyst particle, a numerical value indicated by g/L is an amount obtained by normalizing the mass (g) of the catalyst particle by the volume of the support (L), more specifically, by a total volume including the cell of the honeycomb ceramics and voids in the cell.

In Table 1, the samples in which * is assigned to the sample number are samples that do not satisfy the first requirement or the second requirement of the present invention described above, and the samples in which * is not assigned to the sample number are samples that satisfy both the first requirement and the second requirement of the present invention described above.

The supported catalysts for decomposing an organic substance of sample Nos. 1 to 6 are samples which have the same catalyst composition, but are different in the supported amount of the catalyst. The firing temperature during firing is 950° C. in any case. The supported catalysts for decomposing an organic substance of sample Nos. 2 to 6, which have a film thickness of catalyst-supporting film of 5 μm or more, exhibits a supported amount of catalyst particle of 45 g/L or more, and satisfy the first requirement and the second requirement of the present invention, exhibited a toluene decomposition rate before additional heat treatment of 97% or more which was high, and a deterioration rate of the toluene decomposition rate after additional heat treatment of less than 10%, more specifically, 0.5% or less.

Here, the deterioration rate of the toluene decomposition rate being less than 10% is equivalent to "the decomposition rate of an organic substance after a supported catalyst for decomposing an organic substance is heat-treated at 950° C. for 48 hours being greater than 0.9 when the decomposition rate before heat treatment is defined as 1".

On the other hand, the supported catalyst for decomposing an organic substance of sample No. 1, which has a film thickness of catalyst-supporting film of 1 μm, exhibits a supported amount of catalyst particle of 20 g/L, and do not satisfy the first requirement or the second requirement of the present invention, exhibited a toluene decomposition rate before additional heat treatment of 61.2%, which was low, and a deterioration rate of the toluene decomposition rate after additional heat treatment of 20.6%, which was higher than 10%.

The supported catalysts for decomposing an organic substance of sample Nos. 7 to 12 are samples which have the same catalyst composition, but are different in the supported amount of the catalyst. The firing temperature during firing is 1,050° C. in any case. The supported catalysts for decomposing an organic substance of sample Nos. 8 to 12, which have a film thickness of catalyst-supporting film of 5 μm or more, exhibit a supported amount of catalyst particle of 45 g/L or more, and satisfy the first requirement and the second requirement of the present invention, exhibited a toluene decomposition rate before additional heat treatment of 96% or more, which was high, and a deterioration rate after additional heat treatment of less than 10%, more specifically, 0.9% or less.

On the other hand, the supported catalyst for decomposing an organic substance of sample No. 7, which has a film thickness of catalyst-supporting film of 2 μm, exhibits a supported amount of catalyst particle of 38 g/L, and do not satisfy the first requirement or the second requirement of the present invention, exhibited a deterioration rate after additional heat treatment of 14.4%, which was higher than 10%.

That is, in the supported catalyst for decomposing an organic substance that has a film thickness of catalyst-supporting film of 5 μm or more and satisfies the first requirement of the present invention, deterioration due to heat treatment at high temperature is sufficiently prevented. As shown in Table 1, the film thickness of the catalyst-supporting film is preferably 116 μm or less.

Further, in the supported catalyst for decomposing an organic substance that exhibits a supported amount of catalyst particle of 45 g/L or more and satisfies the second requirement of the present invention, deterioration due to heat treatment at high temperature is sufficiently prevented. As shown in Table 1, the supported amount of the catalyst particle is preferably 530 g/L or less.

Note that the supported catalysts for decomposing an organic substance of sample Nos. 2 to 6 and 8 to 12 shown in Table 1 satisfy both the first requirement and the second requirement of the present invention, but if at least one of the requirements is satisfied, deterioration due to heat treatment at high temperature is prevented. The same applies to the following description using Tables 2 to 5.

Next, for the purpose of confirming characteristics in a case of changing the firing temperature, supported catalysts for decomposing an organic substance of sample Nos. 13 to 15 shown in Table 2 were prepared. The evaluation method of the prepared supported catalysts for decomposing an organic substance was the same as the above-described evaluation method.

TABLE 2

| Sample No. | Catalyst Preparation compositional ratio | | | | A(x) | | B(y) | M(z) | | | | Catalyst slurry Compound | Pure water |
|---|---|---|---|---|---|---|---|---|---|---|---|---|---|
| | x | y | z | y + z | Ba | Sr | Zr | Mn | Co | Ni | Fe | g | g |
| 13 | 1.010 | 0.900 | 0.100 | 1.000 | 1.000 | | 1.000 | 1.000 | | | | 450 | 300 |
| 14 | 1.010 | 0.900 | 0.100 | 1.000 | 1.000 | | 1.000 | 1.000 | | | | 450 | 320 |
| 4 | 1.010 | 0.900 | 0.100 | 1.000 | 1.000 | | 1.000 | 1.000 | | | | 450 | 320 |
| 10 | 1.010 | 0.900 | 0.100 | 1.000 | 1.000 | | 1.000 | 1.000 | | | | 450 | 320 |
| 15 | 1.010 | 0.900 | 0.100 | 1.000 | 1.000 | | 1.000 | 1.000 | | | | 450 | 320 |

| | | Before additional heat treatment | | | After additional heat treatment | |
|---|---|---|---|---|---|---|
| | | Supported amount of catalyst | | Decomposition | Decomposition | Deterioration |
| Sample No. | Firing temperature | g/L | Film thickness | rate % | rate % | rate % |
| 13 | 500° C. | 191 | 35 | 99.2 | 99 | 0.2 |
| 14 | 800° C. | 195 | 34 | 99.1 | 99 | 0.1 |
| 4 | 950° C. | 193 | 35 | 99.4 | 99.4 | 0.0 |
| 10 | 1050° C. | 200 | 36 | 97.9 | 97.6 | 0.3 |
| 15 | 1150° C. | 191 | 38 | 78.4 | 71.3 | 9.1 |

As shown in Table 2, the supported catalysts for decomposing an organic substance of sample Nos. 4, 10, and 13 to 15 have the same catalyst composition, but are different in firing temperature during firing. A difference in supported amount of the catalyst particle and film thickness is 10% or less. These supported catalysts for decomposing an organic substance have a film thickness of catalyst-supporting film of 5 μm or more, exhibit a supported amount of catalyst particle of 45 g/L or more, and satisfy the first requirement and the second requirement of the present invention.

As shown in Table 2, the supported catalyst for decomposing an organic substance of sample Nos. 4, 10, and 13 to 15 exhibited a deterioration rate after additional heat treatment of less than 10%. Particularly, if the firing temperature during firing is 1,050° C. or lower, the deterioration rate after additional heat treatment does not significantly change even when the firing temperature is changed. Accordingly, considering the results shown in Table 1, if the firing temperature during firing is 1,050° C. or lower, deterioration due to heat treatment at high temperature is considered to be sufficiently prevented when the film thickness of the catalyst-supporting film is 5 μm or more, or the supported amount of the catalyst particle is 45 g/L or more.

Here, as shown in Table 2, if the firing temperature during firing is 1,050° C. or lower, the deterioration rate after additional heat treatment was 0.3% or less, which is low. However, the supported catalyst for decomposing an organic substance of sample No. 15, in which the firing temperature was 1,150° C., exhibited a deterioration rate after additional heat treatment of 9.1%. The reason for this is that, in the case where the firing temperature is as high as 1,150° C., chemical reaction occurs between the support and the catalyst with decrease in specific surface area of the catalyst, thus decreasing the decomposition rate. For this reason, the firing temperature when preparing the supported catalyst for decomposing an organic substance is preferably 1,050° C. or lower.

Next, for the purpose of confirming characteristics in a case of changing the composition of the catalyst, supported catalysts for decomposing an organic substance of sample Nos. 16 to 29 shown in Table 3 were prepared. The evaluation method of the prepared supported catalysts for decomposing an organic substance was the same as the above-described evaluation method. Note that the firing temperature for all the supported catalysts for decomposing an organic substance shown in Table 3 is 950° C.

TABLE 3

| Sample No. | Catalyst Preparation compositional ratio | | | | A(x) | | B(y) | M(z) | | | | Catalyst slurry Compound | Pure water |
|---|---|---|---|---|---|---|---|---|---|---|---|---|---|
| | x | y | z | y + z | Ba | Sr | Zr | Mn | Co | Ni | Fe | g | g |
| 16 | 0.995 | 0.900 | 0.100 | 1.000 | 1.000 | | 1.000 | 1.000 | | | | 450 | 320 |
| 17 | 1.000 | 0.900 | 0.100 | 1.000 | 1.000 | | 1.000 | 1.000 | | | | 450 | 320 |
| 18 | 1.001 | 0.900 | 0.100 | 1.000 | 1.000 | | 1.000 | 1.000 | | | | 450 | 320 |
| 19 | 1.005 | 0.900 | 0.100 | 1.000 | 1.000 | | 1.000 | 1.000 | | | | 450 | 320 |
| 4 | 1.010 | 0.900 | 0.100 | 1.000 | 1.000 | | 1.000 | 1.000 | | | | 450 | 320 |
| 20 | 1.050 | 0.900 | 0.100 | 1.000 | 1.000 | | 1.000 | 1.000 | | | | 450 | 320 |
| 21 | 1.100 | 0.900 | 0.100 | 1.000 | 1.000 | | 1.000 | 1.000 | | | | 450 | 320 |
| 22 | 1.001 | 0.980 | 0.020 | 1.000 | 1.000 | | 1.000 | 1.000 | | | | 450 | 320 |
| 23 | 1.001 | 0.950 | 0.050 | 1.000 | 1.000 | | 1.000 | 1.000 | | | | 450 | 320 |
| 18 | 1.001 | 0.900 | 0.100 | 1.000 | 1.000 | | 1.000 | 1.000 | | | | 450 | 320 |
| 24 | 1.001 | 0.800 | 0.200 | 1.000 | 1.000 | | 1.000 | 1.000 | | | | 450 | 320 |
| 25 | 1.001 | 0.600 | 0.400 | 1.000 | 1.000 | | 1.000 | 1.000 | | | | 450 | 320 |
| 26 | 1.050 | 0.980 | 0.020 | 1.000 | 1.000 | | 1.000 | 1.000 | | | | 450 | 320 |

TABLE 3-continued

| 27 | 1.050 | 0.950 | 0.050 | 1.000 | 1.000 | 1.000 | 1.000 | 450 | 320 |
| 20 | 1.050 | 0.900 | 0.100 | 1.000 | 1.000 | 1.000 | 1.000 | 450 | 320 |
| 28 | 1.050 | 0.800 | 0.200 | 1.000 | 1.000 | 1.000 | 1.000 | 450 | 320 |
| 29 | 1.050 | 0.600 | 0.400 | 1.000 | 1.000 | 1.000 | 1.000 | 450 | 320 |

| | | Before additional heat treatment | | | After additional heat treatment | |
| --- | --- | --- | --- | --- | --- | --- |
| | | Supported amount of catalyst | | Decomposition | Decomposition | Deterioration |
| Sample No. | Firing temperature | g/L | Film thickness | rate % | rate % | rate % |
| 16 | 950° C. | 201 | 37 | 94.8 | 87.2 | 8.0 |
| 17 | 950° C. | 192 | 34 | 97.7 | 93.6 | 4.2 |
| 18 | 950° C. | 198 | 35 | 98.9 | 97.6 | 1.3 |
| 19 | 950° C. | 192 | 35 | 99.2 | 99 | 0.2 |
| 4 | 950° C. | 193 | 35 | 99.4 | 99.4 | 0.0 |
| 20 | 950° C. | 210 | 39 | 98.9 | 98.9 | 0.0 |
| 21 | 950° C. | 231 | 44 | 89.5 | 89.4 | 0.1 |
| 22 | 950° C. | 204 | 38 | 86.7 | 85.3 | 1.6 |
| 23 | 950° C. | 202 | 37 | 97.3 | 96.1 | 1.2 |
| 18 | 950° C. | 198 | 35 | 98.9 | 97.6 | 1.3 |
| 24 | 950° C. | 195 | 35 | 98.9 | 97.5 | 1.4 |
| 25 | 950° C. | 162 | 29 | 95.8 | 90.4 | 5.6 |
| 26 | 950° C. | 221 | 42 | 89.2 | 89 | 0.2 |
| 27 | 950° C. | 209 | 40 | 98.4 | 98.3 | 0.1 |
| 20 | 950° C. | 210 | 39 | 98.9 | 98.9 | 0.0 |
| 28 | 950° C. | 198 | 37 | 99.3 | 98.6 | 0.7 |
| 29 | 950° C. | 178 | 33 | 98.8 | 95.7 | 3.1 |

The supported catalysts for decomposing an organic substance of sample Nos. 16 to 21, and 4 are samples in which the composition y is 0.900, the composition z is 0.100, and the composition x is changed in a range of 0.995 to 1.100. All of the supported catalysts for decomposing an organic substance of sample Nos. 4, and 16 to 21, which satisfy the first requirement and the second requirement of the present invention, exhibited a deterioration rate after additional heat treatment of less than 10%, more specifically, 8.0% or less.

In other words, in a case where the composition x is changed in a range of 1.000 to 1.100 with the supported catalyst for decomposing an organic substance of sample No. 4 being a reference, there is no significant variation such that the deterioration rate after additional heat treatment is greater than 10%, and it is therefore found that deterioration due to heat treatment at high temperature can be prevented. The supported catalysts for decomposing an organic substance of sample Nos. 16 to 21 have a film thickness of catalyst-supporting film of 34 μm to 44 μm and exhibits a supported amount of catalyst particle of 192 g/L to 231 g/L. Considering the results shown in Table 1, it is conceived that when the film thickness of the catalyst-supporting film is 5 μm or more, or the supported amount of the catalyst particle is 45 g/L or more, deterioration due to heat treatment at high temperature can be effectively prevented.

The supported catalysts for decomposing an organic substance of sample Nos. 22 to 25, and 18 are samples in which the composition x is 1.001, and the composition y is changed in a range of 0.600 to 0.980 (the composition z is changed in a range of 0.020 to 0.400) while the relationship y+z=1 is maintained. The supported catalysts for decomposing an organic substance of sample Nos. 18 and 22 to 25 which satisfy the first requirement and the second requirement of the present invention, exhibited a deterioration rate after additional heat treatment of less than 10%, more specifically, 5.6% or less.

In other words, even in a case where the composition x is fixed to 1.001, and the composition y is changed in a range of 0.600 to 0.980 (the composition z is changed in a range of 0.020 to 0.400) while the relationship y+z=1 is maintained, there is no significant variation such that the deterioration rate after additional heat treatment is greater than 10%, and it is therefore found that deterioration due to heat treatment at high temperature can be prevented. The supported catalysts for decomposing an organic substance of sample Nos. 22 to 25 have a film thickness of catalyst-supporting film of 29 μm to 38 μm, and exhibits a supported amount of catalyst particle of 162 g/L to 204 g/L. Considering the results shown in Table 1, it is conceived that when the film thickness of the catalyst-supporting film is 5 μm or more, or the supported amount of the catalyst particle is 45 g/L or more, deterioration due to heat treatment at high temperature can be effectively prevented.

The supported catalysts for decomposing an organic substance of sample Nos. 26 to 29, and 20 are samples in which the composition x is 1.050, and the composition y is changed in a range of 0.600 to 0.980 (the composition z is changed in a range of 0.020 to 0.400) while the relationship y+z=1 is maintained. The supported catalysts for decomposing an organic substance of sample Nos. 20 and 26 to 29, which satisfy the first requirement and the second requirement of the present invention, exhibited a deterioration rate after additional heat treatment of less than 10%, more specifically, 3.1% or less.

In other words, even in a case where the composition x is fixed to 1.050, and the composition y is changed in a range of 0.600 to 0.980 (the composition z is changed in a range of 0.020 to 0.400) while the relationship y+z=1 is maintained, there is no significant variation such that the deterioration rate after additional heat treatment is greater than 10%, and it is therefore found that deterioration due to heat treatment at high temperature can be prevented. The supported catalysts for decomposing an organic substance of sample Nos. 26 to 29 have a film thickness of catalyst-supporting film of 33 μm to 42 μm, and exhibit a supported amount of catalyst particle of 178 g/L to 221 g/L. Considering the results shown in Table 1, it is conceived that when the film thickness of the catalyst-supporting film is 5 μm or more, or the supported amount of the catalyst particle is 45 g/L or more, deterioration due to heat treatment at high temperature can be effectively prevented.

As described above, the supported catalyst for decomposing an organic substance that satisfy the first requirement or the second requirement of the present invention can prevent deterioration due to heat treatment at high temperature not only in a case where the composition x, the composition y, and the composition z are values shown in Table 1, but also in a case where these compositions are changed as shown in Table 2.

Further, among the supported catalysts for decomposing an organic substance that satisfy the first requirement or the second requirement of the present invention, the supported catalysts for decomposing an organic substance of sample Nos. 4, 18 to 20, 22 to 24, and 26 to 28, in which the composition x satisfies the relationship $1.001 \leq x \leq 1.05$ and the composition z satisfies the relationship $0.05 \leq z \leq 0.2$, exhibit a toluene decomposition rate before additional heat treatment of 85% to a deterioration rate after additional heat treatment of 3% or less, more specifically, 1.6% or less.

Thus, in the supported catalyst for decomposing an organic substance that satisfies the first requirement or the second requirement of the present invention, it is preferred that the composition x satisfies the relationship $1.001 \leq x \leq 1.05$, and the composition z satisfies the relationship $0.05 \leq z \leq 0.2$.

Moreover, among the supported catalysts for decomposing an organic substance that satisfy the above-described relationship ($1.001 \leq x \leq 1.05$, and $0.05 \leq z \leq 0.2$), the supported catalysts for decomposing an organic substance of sample Nos. 4, 19, 20, and 26 to 28, in which the composition x satisfies the relationship $x \geq 1.005$, exhibit a deterioration rate after additional heat treatment of 0.7% or less, which is further low.

Thus, in the supported catalyst for decomposing an organic substance in which the composition x satisfies the relationship $1.001 \leq x \leq 1.05$ and the composition z satisfies the relationship $0.05 \leq z \leq 0.2$, it is preferred that the composition x satisfies the relationship $x \geq 1.005$.

Moreover, it is found that, among the supported catalysts for decomposing an organic substance of sample Nos. 4 and 16 to 21 in which the composition y and the composition z are the same, the supported catalysts for decomposing an organic substance of sample Nos. 4, and 19 to 21, in which the composition x satisfies the relationship $x \geq 1.005$, exhibit a deterioration rate after additional heat treatment of 0.2% or less, which is low. In other words, if the composition y and the composition z are the same, it is preferred that the composition x satisfies the relationship $x \geq 1.005$.

Moreover, among the supported catalysts for decomposing an organic substance that satisfy the above-described relationship ($1.001 \leq x \leq 1.05$, and $0.05 \leq z \leq 0.2$), the supported catalysts for decomposing an organic substance of sample Nos. 4, 18 to 20, 22, 23, 26, and 27, in which the composition z satisfies the relationship $z \leq 0.1$, exhibit a deterioration rate after additional heat treatment of 1.6% or less.

Thus, in the supported catalyst for decomposing an organic substance in which the composition x satisfies the relationship $1.001 \leq x \leq 1.05$ and the composition z satisfies the relationship $0.05 \leq z \leq 0.2$, it is preferred that the composition z satisfies the relationship $z \leq 0.1$.

Moreover, among the supported catalysts for decomposing an organic substance of sample Nos. 20 and 26 to 29 in which the composition x is the same, the supported catalysts for decomposing an organic substance of sample Nos. 20, 26, and 27 in which the composition z satisfies the relationship $z \leq 0.1$, exhibit a deterioration rate after additional heat treatment of 0.2% or less, which is further low. In other words, if the composition x is the same, it is preferred that the composition z satisfies the relationship $z \leq 0.1$.

Next, for the purpose of confirming characteristics in a case of changing the constituent elements of the catalyst, supported catalysts for decomposing an organic substance of sample Nos. 30 to 39 shown in Table 4 were prepared. Here, in addition to the raw material powder used when preparing the supported catalysts for decomposing an organic substance of sample Nos. 1 to 12 in Table 1, high-purity $Co_3O_4$ powder, NiO powder, and $Fe_2O_3$ powder were prepared, and perovskite-type composite oxides were then prepared so as to be the compositions in Table 4.

Further, in the process of preparing a catalyst slurry for supporting, the amounts of the perovskite-type compound and pure water were changed to the amounts shown in Table 5 according to the composition. The evaluation method of the prepared supported catalysts for decomposing an organic substance was the same as the above-described evaluation method. Note that the firing temperature for all the supported catalysts for decomposing an organic substance shown in Table 4 is 950° C.

TABLE 4

| Sample No. | Catalyst | | | | | | | | | | | Catalyst slurry | |
|---|---|---|---|---|---|---|---|---|---|---|---|---|---|
| | Preparation compositional ratio | | | | A(x) | | B(y) | M(z) | | | | Compound | Pure water |
| | x | y | z | y + z | Ba | Sr | Zr | Mn | Co | Ni | Fe | g | g |
| 30 | 1.000 | 0.900 | 0.100 | 1.000 | 1.000 | | 1.000 | | 1.000 | | | 450 | 320 |
| 31 | 1.001 | 0.900 | 0.100 | 1.000 | 1.000 | | 1.000 | | 1.000 | | | 450 | 320 |
| 32 | 1.005 | 0.900 | 0.100 | 1.000 | 1.000 | | 1.000 | | 1.000 | | | 450 | 320 |
| 33 | 1.005 | 0.800 | 0.200 | 1.000 | 1.000 | | 1.000 | | 1.000 | | | 450 | 320 |
| 34 | 1.005 | 0.600 | 0.400 | 1.000 | 1.000 | | 1.000 | | 1.000 | | | 450 | 320 |
| 35 | 1.000 | 0.900 | 0.100 | 1.000 | 1.000 | | 1.000 | 0.400 | 0.400 | 0.100 | 0.100 | 450 | 320 |
| 36 | 1.001 | 0.900 | 0.100 | 1.000 | 1.000 | | 1.000 | 0.400 | 0.400 | 0.100 | 0.100 | 450 | 320 |
| 37 | 1.005 | 0.900 | 0.100 | 1.000 | 1.000 | | 1.000 | 0.400 | 0.400 | 0.100 | 0.100 | 450 | 320 |
| 38 | 1.005 | 0.800 | 0.200 | 1.000 | 1.000 | | 1.000 | 0.400 | 0.400 | 0.100 | 0.100 | 450 | 320 |
| 39 | 1.005 | 0.600 | 0.400 | 1.000 | 1.000 | | 1.000 | 0.400 | 0.400 | 0.100 | 0.100 | 450 | 320 |

TABLE 4-continued

| | | Before additional heat treatment | | | After additional heat treatment | |
| | | Supported amount of catalyst | | Decomposition | Decomposition | Deterioration |
| Sample No. | Firing temperature | g/L | Film thickness | rate % | rate % | rate % |
| --- | --- | --- | --- | --- | --- | --- |
| 30 | 950° C. | 188 | 38 | 96.3 | 93.3 | 3.1 |
| 31 | 950° C. | 192 | 37 | 96.6 | 94.9 | 1.8 |
| 32 | 950° C. | 190 | 37 | 97.1 | 95.8 | 1.3 |
| 33 | 950° C. | 190 | 36 | 98.5 | 96.7 | 1.8 |
| 34 | 950° C. | 195 | 38 | 96.3 | 91.4 | 5.1 |
| 35 | 950° C. | 190 | 33 | 94.6 | 90.9 | 3.9 |
| 36 | 950° C. | 185 | 35 | 95.1 | 93.7 | 1.5 |
| 37 | 950° C. | 193 | 34 | 95.9 | 95.2 | 0.7 |
| 38 | 950° C. | 196 | 34 | 97.1 | 95.8 | 1.3 |
| 39 | 950° C. | 189 | 33 | 93.5 | 89.2 | 4.6 |

The supported catalysts for decomposing an organic substance of sample Nos. 30 to 34 are samples which are produced using $Co_3O_4$ powder in place of $MnCO_3$ powder, and in which M of the perovskite-type composite oxide represented by the general formula $A_xB_yM_zO_w$ is not Mn but Co. The supported catalysts for decomposing an organic substance of sample Nos. of 30 to 34 are samples which satisfy the first requirement and the second requirement of the present invention. In these supported catalyst for organic substance decomposition, the deterioration rate after additional heat treatment was less than 10%, more specifically, 5.1% or less.

That is, it is found that even in a case where M of the perovskite-type composite oxide represented by the general formula $A_xB_yM_zO_w$ is not Mn but Co, there is no significant variation such that the deterioration rate after additional heat treatment is greater than 10%, and thus deterioration due to heat treatment at high temperature can be prevented. The supported catalysts for decomposing an organic substance of sample Nos. 30 to 34 have a film thickness of catalyst-supporting film of 36 μm to 38 μm, and a supported amount of catalyst particle of 188 g/L to 195 g/L. Considering the results shown in Table 1, it is conceived that when the film thickness of the catalyst-supporting film is 5 μm or more, or the supported amount of the catalyst particle is 45 g/L or more, deterioration due to heat treatment at high temperature can be effectively prevented.

The supported catalysts for decomposing an organic substance of sample Nos. 35 to 39 are samples which are produced using high-purity $Co_3O_4$ powder, NiO powder, and $Fe_2O_3$ powder in addition to the raw material powder used when preparing the supported catalysts for decomposing an organic substance of sample Nos. 1 to 12 in Table 1 and in which M of the perovskite-type composite oxide represented by the general formula $A_xB_yM_zO_w$ contains Mn, Co, Ni, and Fe. The supported catalysts for decomposing an organic substance of sample Nos. of 35 to 39 are samples which satisfy the first requirement and the second requirement of the present invention. These supported catalysts for decomposing an organic substance exhibited a deterioration rate after additional heat treatment of less than 10%, more specifically, 4.6% or less.

That is, even in a case where M of the perovskite-type composite oxide represented by the general formula $A_xB_yM_zO_w$ contains Mn, Co, Ni, and Fe, there is no significant variation such that the deterioration rate after additional heat treatment is greater than 10%, and it is therefore found that deterioration due to heat treatment at high temperature can be prevented. The supported catalysts for decomposing an organic substance of sample Nos. 35 to 39 have a film thickness of catalyst-supporting film of 33 μm to 35 μm, and exhibit a supported amount of catalyst particle of 189 g/L to 196 g/L. Considering the results shown in Table 1, it is conceived that when the film thickness of the catalyst-supporting film is 5 μm or more, or the supported amount of the catalyst particle is 45 g/L or more, deterioration due to heat treatment at high temperature can be effectively prevented.

Further, among the supported catalysts for decomposing an organic substance that satisfy the first requirement or the second requirement of the present invention, the supported catalysts for decomposing an organic substance of sample Nos. 31 to 33 and 36 to 38 in which the composition x satisfies the relationship $1.001 \leq x \leq 1.05$ and the composition z satisfies the relationship $0.05 \leq z \leq 0.2$, exhibit a toluene decomposition rate before additional heat treatment of 85% or more, and a deterioration rate after additional heat treatment of 3% or less, more specifically, 1.8% or less, which is further low.

Thus, in the supported catalyst for decomposing an organic substance that satisfies the first requirement or the second requirement of the present invention, it is preferred that the composition x satisfies the relationship $1.001 \leq x \leq 1.05$, and the composition z satisfies the relationship $0.05 \leq z \leq 0.2$.

Moreover, focusing on the supported catalysts for decomposing an organic substance of sample Nos. 36 to 38 in which the composition x satisfies the relationship $1.001 \leq x \leq 1.05$ and the composition z satisfies the relationship $0.05 \leq z \leq 0.2$, the supported catalysts for decomposing an organic substance of sample Nos. 37 and 38, in which the composition x satisfies the relationship $x \geq 1.005$, exhibit a deterioration rate after additional heat treatment of 1.3% or less, which is further low. Thus, in the supported catalyst for decomposing an organic substance in which the composition x satisfies the relationship $1.001 \leq x \leq 1.05$ and the composition z satisfies the relationship $0.05 \leq z \leq 0.2$, it is preferred that the composition x satisfies the relationship $x \geq 1.005$.

Also, among the supported catalysts for decomposing an organic substance of sample Nos. 30 to 32 in which the composition y and the composition z are the same, the supported catalyst for decomposing an organic substance of sample No. 32, in which the composition x satisfies the relationship $x \geq 1.005$, exhibits the lowest deterioration rate after additional heat treatment. Similarly, among the supported catalysts for decomposing an organic substance of sample Nos. 35 to 37 in which the composition y and the composition z are the same, the supported catalyst for decomposing an organic substance of sample No. 37, in which the composition x satisfies the relationship x≥1.005, exhibits the lowest deterioration rate after additional heat treatment. Accordingly, if the composition y and the composition z are the same, it is preferred that the composition x satisfies the relationship x≥1.005.

and perovskite-type composite oxides were then prepared so as to be the compositions in Table 5.

Further, in the process of preparing a catalyst slurry for supporting, the amounts of the perovskite-type compound and pure water were changed to the amounts shown in Table 5 according to the composition. The evaluation method of the prepared supported catalysts for decomposing an organic substance was the same as the above-described evaluation method. Note that the firing temperature for all the supported catalysts for decomposing an organic substance shown in Table 5 is 950° C.

TABLE 5

| Sample No. | Catalyst | | | | | | | | | | | Catalyst slurry | |
|---|---|---|---|---|---|---|---|---|---|---|---|---|---|
| | Preparation compositional ratio | | | | A(x) | B(y) | | M(z) | | | | Compound | Pure water |
| | x | y | z | y + z | Ba | Sr | Zr | Mn | Co | Ni | Fe | g | g |
| 40 | 1.000 | 0.900 | 0.100 | 1.000 | | 1.000 | 1.000 | 1.000 | | | | 370 | 320 |
| 41 | 1.001 | 0.900 | 0.100 | 1.000 | | 1.000 | 1.000 | 1.000 | | | | 370 | 320 |
| 42 | 1.005 | 0.900 | 0.100 | 1.000 | | 1.000 | 1.000 | 1.000 | | | | 370 | 320 |
| 43 | 1.005 | 0.800 | 0.200 | 1.000 | | 1.000 | 1.000 | 1.000 | | | | 370 | 320 |
| 44 | 1.005 | 0.600 | 0.400 | 1.000 | | 1.000 | 1.000 | 1.000 | | | | 370 | 320 |
| 45 | 1.000 | 0.900 | 0.100 | 1.000 | 0.500 | 0.500 | 1.000 | 0.700 | 0.200 | 0.050 | 0.050 | 400 | 320 |
| 46 | 1.001 | 0.900 | 0.100 | 1.000 | 0.500 | 0.500 | 1.000 | 0.700 | 0.200 | 0.050 | 0.050 | 400 | 320 |
| 47 | 1.005 | 0.900 | 0.100 | 1.000 | 0.500 | 0.500 | 1.000 | 0.700 | 0.200 | 0.050 | 0.050 | 400 | 320 |
| 48 | 1.005 | 0.800 | 0.200 | 1.000 | 0.500 | 0.500 | 1.000 | 0.700 | 0.200 | 0.050 | 0.050 | 400 | 320 |
| 49 | 1.005 | 0.600 | 0.400 | 1.000 | 0.500 | 0.500 | 1.000 | 0.700 | 0.200 | 0.050 | 0.050 | 400 | 320 |

| | | Before additional heat treatment | | | After additional heat treatment | |
|---|---|---|---|---|---|---|
| | | Supported amount of catalyst | | Decomposition | Decomposition | Deterioration |
| Sample No. | Firing temperature | g/L | Film thickness | rate % | rate % | rate % |
| 40 | 950° C. | 157 | 36 | 90.6 | 87.5 | 3.4 |
| 41 | 950° C. | 152 | 39 | 91.1 | 90 | 1.2 |
| 42 | 950° C. | 155 | 35 | 92.1 | 91.4 | 0.8 |
| 43 | 950° C. | 156 | 38 | 95.5 | 93.2 | 2.4 |
| 44 | 950° C. | 158 | 38 | 91.6 | 85.4 | 6.8 |
| 45 | 950° C. | 173 | 35 | 94.9 | 91.7 | 3.4 |
| 46 | 950° C. | 171 | 38 | 95.4 | 94.1 | 1.4 |
| 47 | 950° C. | 169 | 36 | 96.7 | 95.6 | 1.1 |
| 48 | 950° C. | 169 | 36 | 98.4 | 97.2 | 1.2 |
| 49 | 950° C. | 171 | 36 | 96.1 | 92 | 4.3 |

Also, among the supported catalysts for decomposing an organic substance of sample Nos. 32 to 34 in which the composition x is the same, the supported catalyst for decomposing an organic substance of sample No. 32, in which the composition z satisfies the relationship z≤0.1, exhibits the lowest deterioration rate after additional heat treatment. Similarly, among the supported catalysts for decomposing an organic substance of sample Nos. 37 to 39 in which the composition x is the same, the supported catalyst for decomposing an organic substance of sample No. 37, in which the composition z satisfies the relationship z≤0.1, exhibits the lowest deterioration rate after additional heat treatment. In other words, if the composition x is the same, it is preferred that the composition z satisfies the relationship z≤0.1.

Next, for the purpose of confirming characteristics in a case of changing the constituent elements of the catalyst, supported catalysts for decomposing an organic substance of sample Nos. 40 to 49 shown in Table 5 were prepared. Here, in addition to the raw material powder used when preparing the supported catalysts for decomposing an organic substance of sample Nos. 1 to 12 in Table 1 and sample Nos. 35 to 39 in Table 4, high-purity $SrCO_3$ powder was prepared, The supported catalysts for decomposing an organic substance of sample Nos. 40 to 44 are samples in which A of the perovskite-type composite oxide represented by the general formula $A_xB_yM_zO_w$ is not Ba but Sr and which satisfies the first requirement and the second requirement of the present invention. These supported catalysts for decomposing an organic substance exhibited a toluene decomposition rate before additional heat treatment of 90% or more and a deterioration rate after additional heat treatment of less than 10%, more specifically, 6.8% or less.

That is, even in a case where A of the perovskite-type composite oxide represented by the general formula $A_xB_yM_zO_w$ is not Ba but Sr, there is no significant variation such that the deterioration rate after additional heat treatment is greater than 10%, and it is therefore found that deterioration due to heat treatment at high temperature can be prevented. The supported catalysts for decomposing an organic substance of sample Nos. 40 to 44 have a film thickness of catalyst-supporting film of 35 μm to 39 μm and exhibit a supported amount of catalyst particle of 152 g/L to 158 g/L. Considering the results shown in Table 1, it is conceived that when the film thickness of the catalyst-supporting film is 5 μm or more, or the supported amount of the catalyst particle is 45 g/L or more, deterioration due to heat treatment at high temperature can be effectively prevented.

The supported catalysts for decomposing an organic substance of sample Nos. 45 to 49 are samples in which A of the perovskite-type composite oxide represented by the general formula $A_xB_yM_zO_w$ contains Ba and Sr, B contains Zr, and M contains Mn, Co, Ni, and Fe, and which satisfy the first requirement and the second requirement of the present invention. These supported catalysts for decomposing an organic substance exhibited a toluene decomposition rate before additional heat treatment of 94% or more and a deterioration rate after additional heat treatment of less than 10%, more specifically, 4.3% or less.

That is, even in a case where A of the perovskite-type composite oxide represented by the general formula $A_xB_yM_zO_w$ contains Ba and Sr, B contains Zr, and M contains Mn, Co, Ni, and Fe, there is no significant variation such that the deterioration rate after additional heat treatment is greater than 10%, and it is therefore found that deterioration due to heat treatment at high temperature can be prevented. The supported catalysts for decomposing an organic substance of sample Nos. 45 to 49 have a film thickness of catalyst-supporting film of 35 μm to 38 μm, and exhibit a supported amount of catalyst particle of 169 g/L to 173 g/L. Considering the results shown in Table 1, it is conceived that when the film thickness of the catalyst-supporting film is 5 μm or more, or the supported amount of the catalyst particle is 45 g/L or more, deterioration due to heat treatment at high temperature can be effectively prevented.

Further, among the supported catalysts for decomposing an organic substance that satisfy the first requirement or the second requirement of the present invention, the supported catalysts for decomposing an organic substance of sample Nos. 41 to 43 and 46 to 48, in which the composition x satisfies the relationship $1.001 \leq x \leq 1.05$ and the composition z satisfies the relationship $0.05 \leq z \leq 0.2$, exhibit a toluene decomposition rate before additional heat treatment of 85% or more and a deterioration rate after additional heat treatment of 3% or less, more specifically, 2.4% or less.

Thus, in the supported catalyst for decomposing an organic substance that satisfies the first requirement or the second requirement of the present invention, it is preferred that the composition x satisfies the relationship $1.001 \leq x \leq 1.05$, and the composition z satisfies the relationship $0.05 \leq z \leq 0.2$.

Moreover, focusing on the supported catalysts for decomposing an organic substance of sample Nos. 46 to 48 in which the composition x satisfies the relationship $1.001 \leq x \leq 1.05$, and the composition z satisfies the relationship $0.05 \leq z \leq 0.2$, the supported catalysts for decomposing an organic substance of sample Nos. 47 and 48, in which the composition x satisfies the relationship $x \geq 1.005$, exhibit a deterioration rate after additional heat treatment of 1.2% or less, which is further low. Thus, in the supported catalyst for decomposing an organic substance in which the composition x satisfies the relationship $1.001 \leq x \leq 1.05$ and the composition z satisfies the relationship $0.05 \leq z \leq 0.2$, it is preferred that the composition x satisfies the relationship $x \geq 1.005$.

Also, among the supported catalysts for decomposing an organic substance of sample Nos. 40 to 42 in which the composition y and the composition z are the same, the supported catalyst for decomposing an organic substance of sample No. 42, in which the composition x satisfies the relationship $x \geq 1.005$, exhibits the lowest deterioration rate after additional heat treatment. Similarly, among the supported catalysts for decomposing an organic substance of sample Nos. 45 to 47 in which the composition y and the composition z are the same, the supported catalyst for decomposing an organic substance of sample No. 47, in which the composition x satisfies the relationship $x \geq 1.005$, exhibits the lowest deterioration rate after additional heat treatment. Accordingly, if the composition y and the composition z are the same, it is preferred that the composition x satisfies the relationship $x \geq 1.005$.

Also, among the supported catalysts for decomposing an organic substance of sample Nos. 42 to 44 in which the composition x is the same, the supported catalyst for decomposing an organic substance of sample No. 42, in which the composition z satisfies the relationship $z \leq 0.1$, exhibits the lowest deterioration rate after additional heat treatment. Similarly, among the supported catalysts for decomposing an organic substance of sample Nos. 47 to 49 in which the composition x is the same, the supported catalyst for decomposing an organic substance of sample No. 47, in which the composition z satisfies the relationship $z \leq 0.1$, exhibits the lowest deterioration rate after additional heat treatment. In other words, if the composition x is the same, it is preferred that the composition z satisfies the relationship $z \leq 0.1$.

As described above, as shown in Tables 1 to 5, the supported catalyst for decomposing an organic substance that satisfies the first requirement or the second requirement of the present invention can prevent deterioration due to heat treatment at high temperature.

The present invention is not limited to the embodiment described above, but various applications and modifications can be made within the scope of the invention.

DESCRIPTION OF REFERENCE SYMBOLS

10: Honeycomb ceramics
11: Cell
12: Pore
20: Supporting honeycomb sample
40: Test apparatus
41: Tube
42: Heating unit
43: Control unit
44: Gas supply tube
45: Gas discharge tube
46: Toluene supply line
47: Nitrogen supply line
48: Oxygen supply line
49: Sampling line
51: Reaction tube

The invention claimed is:

1. A supported catalyst for decomposing an organic substance, the supported catalyst comprising:
 a support; and
 a catalyst-supporting film supported on the support, the catalyst-supporting film containing a catalyst particle, and the catalyst-supporting film having a film thickness of 5 μm or more, wherein
 the catalyst particle contains a perovskite composite oxide represented by $A_xB_yM_zO_w$, where the A contains at least one selected from Ba and Sr, the B contains Zr, the M is at least one selected from Mn, Co, Ni and Fe, $y+z=1$, $x \geq 0.995$, $z \leq 0.4$, and w is a positive value that satisfies electrical neutrality, and wherein
 the support comprises cordierite.

2. The supported catalyst for decomposing an organic substance according to claim 1, wherein the film thickness of the catalyst-supporting film is 5 µm to 116 µm.

3. The supported catalyst for decomposing an organic substance according to claim 1, wherein $1.001 \leq x \leq 1.05$ and $0.05 \leq z \leq 0.2$.

4. The supported catalyst for decomposing an organic substance according to claim 3, wherein $x \geq 1.005$.

5. The supported catalyst for decomposing an organic substance according to claim 4, wherein $z \leq 0.1$.

6. The supported catalyst for decomposing an organic substance according to claim 3, wherein $z \leq 0.1$.

7. The supported catalyst for decomposing an organic substance according to claim 1, wherein a decomposition rate after the supported catalyst is heat-treated at 950° C. for 48 hours is more than 0.9 when the decomposition rate before the heat treatment is defined as 1.

8. The supported catalyst for decomposing an organic substance according to claim 1, wherein the support is a porous structure containing a plurality of pores, each of the plurality of pores having a diameter of 0.3 µm to 50 µm.

9. An organic substance decomposition device comprising the supported catalyst for decomposing an organic substance according to claim 1.

10. A supported catalyst for decomposing an organic substance, the supported catalyst comprising:
 a support; and
 a catalyst particle supported on the support, wherein
  the catalyst particle contains a perovskite composite oxide represented by $A_xB_yM_zO_w$, where the A contains at least one selected from Ba and Sr, the B contains Zr, the M is at least one selected from Mn, Co, Ni and Fe, $y+z=1$, $x \geq 0.995$, $z \leq 0.4$, and w is a positive value satisfying electrical neutrality, and
  a supported amount as determined by normalizing a mass of the catalyst particle supported on the support by a volume of the support is 45 g/L or more, and wherein the support comprises cordierite.

11. The supported catalyst for decomposing an organic substance according to claim 10, wherein the supported amount is 45 g/L to 530 g/L.

12. The supported catalyst for decomposing an organic substance according to claim 10, wherein $1.001 \leq x \leq 1.05$ and $0.05 \leq z \leq 0.2$.

13. The supported catalyst for decomposing an organic substance according to claim 12, wherein $x \geq 1.005$.

14. The supported catalyst for decomposing an organic substance according to claim 13, wherein $z \leq 0.1$.

15. The supported catalyst for decomposing an organic substance according to claim 12, wherein $z \leq 0.1$.

16. The supported catalyst for decomposing an organic substance according to claim 10, wherein a decomposition rate after the supported catalyst for decomposing an organic substance is heat-treated at 950° C. for 48 hours is more than 0.9 when the decomposition rate before the heat treatment is defined as 1.

17. The supported catalyst for decomposing an organic substance according to claim 10, wherein the support is a porous structure containing a plurality of pores, each of the plurality of pores having a diameter of 0.3 µm to 50 µm.

18. An organic substance decomposition device comprising the supported catalyst for decomposing an organic substance according to claim 10.

* * * * *